(12) United States Patent
Gurjar et al.

(10) Patent No.: US 9,643,914 B2
(45) Date of Patent: May 9, 2017

(54) FINGOLIMOD HYDROCHLORIDE PROCESS

(71) Applicant: Emcure Pharmaceuticals Limited, Pune (IN)

(72) Inventors: Mukund K. Gurjar, Pune (IN); Narendra K. Tripathy, Pune (IN); Kaliaperumal Neelakandan, Pune (IN); Prasad P. Panchabhai, Pune (IN); Nandala Srinivas, Pune (IN); Prabhakaran Balasubramanian, Pune (IN); Sandip B. Buchude, Pune (IN); Balaji R. Mugale, Pune (IN); Pravin P. Ahirrao, Pune (IN); Samit S. Mehta, Pune (IN)

(73) Assignee: EMCURE PHARMACEUTICALS LIMITED, Pune (IN)

( * ) Notice: Subject to any disclaimer, the term of this patent is extended or adjusted under 35 U.S.C. 154(b) by 0 days.

(21) Appl. No.: 15/035,306

(22) PCT Filed: Nov. 14, 2014

(86) PCT No.: PCT/IN2014/000720
§ 371 (c)(1),
(2) Date: May 9, 2016

(87) PCT Pub. No.: WO2015/092809
PCT Pub. Date: Jun. 25, 2015

(65) Prior Publication Data
US 2016/0289166 A1   Oct. 6, 2016

(30) Foreign Application Priority Data

Nov. 25, 2013   (IN) .......................... 3696/MUM/2013

(51) Int. Cl.
*C07C 213/02* (2006.01)
*C07C 215/28* (2006.01)
*C07C 231/12* (2006.01)
*C07C 213/00* (2006.01)

(52) U.S. Cl.
CPC .......... *C07C 213/02* (2013.01); *C07C 213/00* (2013.01); *C07C 215/28* (2013.01); *C07C 231/12* (2013.01); *C07B 2200/07* (2013.01)

(58) Field of Classification Search
None
See application file for complete search history.

(56) References Cited

U.S. PATENT DOCUMENTS

| 6,423,871 B1* | 7/2002 | Jung ..................... C07C 209/08 560/155 |
| 2013/0281739 A1* | 10/2013 | Shrawat ................ C07C 215/28 564/360 |

FOREIGN PATENT DOCUMENTS

WO   WO-2012146980 A2   11/2012

OTHER PUBLICATIONS

Acteone, HPLC grade information sheet: http://www.sigmaaldrich.com/catalog/product/sigald/270725?lang=en&region=US, 2016 (4 pages).*
Siedel et al., Iron-Catalyzed Cross-Coupling Reactions. A Scalable Synthesis of the Immunosuppressive Agent, The Journal of Organic Chemistry, 2004, 69(11):3950-3952.

* cited by examiner

Primary Examiner — Clinton Brooks
(74) Attorney, Agent, or Firm — Blank Rome LLP

(57) ABSTRACT

A process for preparation of diethyl 2-aetamido-2-(4-octyl phenyl)ethyl malonate (III), a key intermediate of fingolimod hydrochloride comprising reaction of 2-(4-octylphenyl) ethyl iodide (IV) with diethyl acetamido malonate in presence of a base and an iodinating agent and in an organic solvent. The compound of formula (III) thus obtained provided fingolimod hydrochloride (Ia) having associated impurities below the regulatory limits.

10 Claims, No Drawings

FINGOLIMOD HYDROCHLORIDE PROCESS

This application is the U.S. national phase of International Patent Application No. PCT/IN2014/000720, filed Nov. 14, 2014, which claims the benefit of Indian Patent Application No. 3696/MUM/2013, filed Nov. 25, 2013.

FIELD OF THE INVENTION

The present invention relates to a process for preparation of fingolimod hydrochloride conforming to regulatory specifications. Specifically, the invention relates to a process for preparation of fingolimod hydrochloride, which is free from associated impurities that are normally encountered during coupling of 2-(4-octylphenyl) ethyl iodide with diethyl acetamidomalonate.

BACKGROUND OF THE INVENTION

Fingolimod (I), chemically known as 2-amino-2-(2-(4-octylphenyl)ethyl)-propan-1,3-diol is a sphingosine 1-phosphate receptor modulator, administered as its hydrochloride salt (Ia) for the treatment of patients with relapsing forms of multiple sclerosis to reduce the frequency of clinical exacerbations and to delay the accumulation of physical disability. Fingolimod hydrochloride capsule with proprietary name 'GILENYA' and strength of 0.50 mg was approved by USFDA on Sep. 21, 2010 for oral administration.

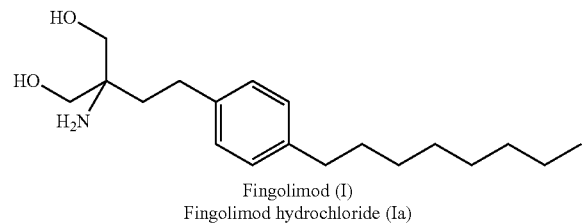 [SMILES: CCCCCCCCc1ccc(CCC(N)(CO)CO)cc1]

Fingolimod (I)
Fingolimod hydrochloride (Ia)

Various researchers have attempted to synthesize fingolimod hydrochloride (Ia). However, these processes were fraught with impurity formation at various stages and more so during the condensation of 2-(4-octylphenyl)ethyl iodide with diethyl acetamidomalonate wherein the associated styrene impurity (II) was usually formed to an extent of 10-15%. This necessitated several purifications for the removal of (II) from the intermediate condensation compound (III) as well as the final product.

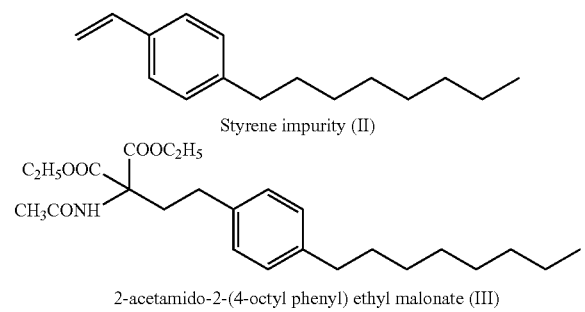

Styrene impurity (II)

2-acetamido-2-(4-octyl phenyl) ethyl malonate (III)

WO 2012146980 and Chemical & Pharmaceutical Bulletin, Vol. 56(4), pages 595-597, 2008 disclose that the prior art methods result in formation of impurity (II) during coupling of 2-(4-octylphenyl) ethyl iodide with diethyl acetamidomalonate in presence of sodium methoxide.

It has been found that the use of base during this step results in high concentration of impurities like styrene (II) and other associated impurities, which eventually gives low yield. The same observation was also made by workers in Synthesis 2000, 4, 505-506.

WO2013111162 discloses a process for preparation of fingolimod containing the regioisomeric impurity (Ib), wherein the disclosed method follows the multi-step process to eliminate the regioisomeric impurity from the fingolimod free base and its hydrochloride.

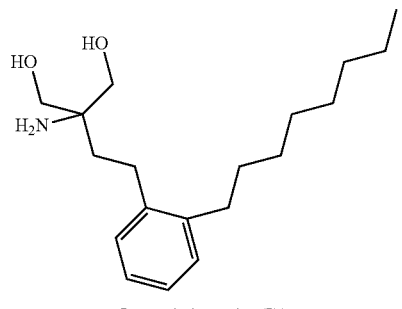

Isomeric impurity (Ib)

In order to circumvent the formation of the styrene impurity, Philippe Durand et. al., (Ref.—Synthesis (2000), (4), 505-506) employed an alternative route involving α-haloacetophenone derivative instead of 2-(4-octylphenyl)ethyl iodide. However, the method required an additional step involving reduction of the carbonyl group of acetophenone derivative in preparing desired intermediate like diethyl-2-acetamido-2-(4-octyl phenyl)ethyl malonate.

Chem. Pharm. Bull. 56(4)-2008, 595-597 discloses another method for minimizing the styrene impurity by subjecting the product containing the styrene impurity to Michael reaction followed by further reduction to yield diethyl 2-acetamido-2-(4-octylphenyl)ethyl malonate, the desired intermediate for preparation of fingolimod. However, this method requires an additional step of Michael reaction followed by reduction, which significantly increases the cost of manufacture on a commercial scale.

Journal of Organic Chemistry 69(11), 3950-3952, (2004) provides a process wherein coupling reaction of 2-(4-octylphenyl) ethyl iodide with diethyl acetamido malonate in N,N-dimethylformamide (DMF) as solvent to eliminate formation of styrene impurity. However, duplication of these experiments reveals that styrene impurity is still formed to the extent of 5-10%.

From the foregoing, it would be evident that there are no prior art methods, which limit or considerably reduce the styrene impurity (II) in a single step and preferably in the same step when it is formed. Therefore, it was necessary to develop a process, which would significantly minimize or eliminate the styrene impurity during the conversion of dimethyl-2-acetamidomalonate to dimethyl-2-acetamido-2-(4-octyl phenyl) ethyl malonate (III) which is then converted to fingolimod. The present invention provides a solution to the above problem by developing an alternative and efficient process to prepare diethyl 2-acetamido-2-(4-octyl phenyl) ethyl malonate (III) intermediate in which the styrene impurity is minimized below regulatory limits and provides fingolimod hydrochloride (Ia) with isomeric and other associated impurities below regulatory limits and without any requirement of column chromatography or repeated crystallization for reducing the impurity and obtaining the desired purity.

OBJECTS OF THE INVENTION

An object of the present invention is to provide an improved process for preparation of fingolimod hydrochloride, which is free from associated impurities and does not utilize column chromatography or other purification methods.

Another object of the present invention is to provide a process for preparation of diethyl-2-acetamido-2-(4-octylphenyl) ethyl malonate (III) free from styrene impurity by utilizing an iodinating agent during reaction of 2-(4-octylphenyl) ethyl iodide with dimethyl 2-acetamidomalonate to obtain diethyl 2-acetamido-2-(4-octyl phenyl) ethyl malonate (III) of desired purity.

Another object of the present invention is to provide a process for preparation of fingolimod hydrochloride free from styrene impurity (II) and isomeric impurity (Ib) without resorting to any additional steps, including purification.

SUMMARY OF THE INVENTION

An aspect of the present invention relates to an improved process for preparation of fingolimod hydrochloride comprising reaction of 2-(4-octylphenyl)ethyl iodide with diethyl acetamidomalonate in presence of a base and an iodinating agent in a solvent to give diethyl-2-acetamido-2-(4-octylphenyl)ethyl malonate (III), which on further reduction and subsequent treatment with hydrochloric acid in an organic solvent gave fingolimod hydrochloride of desired purity.

Another aspect of the present invention relates to a process for the preparation of diethyl-2-acetamido-2-(4-octylphenyl)ethyl malonate (III) comprising reaction of 2-(4-octylphenyl) ethyl iodide with diethyl acetamidomalonate in an organic solvent and in presence of an inorganic base and an iodinating agent, reducing the resulting compound (III) with a metal borohydride followed by subsequent hydrolysis and isolation of fingolimod hydrochloride conforming to regulatory specifications.

DETAILED DESCRIPTION OF THE INVENTION

The present inventors while trying to develop a process for reducing substantially the styrene impurity (II) during the coupling reaction of 2-(4-octylphenyl)ethyl iodide (IV) with diethyl acetamidomalonate in presence of a base like metal carbonates and in an organic solvent unexpectedly found during experimentation that the presence of an iodinating agent during the reaction substantially suppressed the formation of styrene impurity (II) and reduced it below regulatory limits.

This is in stark contrast to prior art methods, wherein it was very difficult to restrict the formation of styrene impurity (II) during the preparation of intermediate (III) and further it was extremely difficult to reduce it during purification without compromising on yield. The present inventors observed that the styrene impurity was formed during the reaction, irrespective of the base used. The product (III) had to undergo repeated crystallization and sometimes chromatographic purification for eliminating impurity (II).

The method embodied in the present invention involves reaction of 2-(4-octylphenyl)-ethyl iodide (IV) with diethyl acetamidomalonate, in presence of a base and an iodinating agent and in an organic solvent.

It was found by the inventors that the formation of the styrene impurity of formula (II) was arrested in presence of the iodinating agent selected from the group of quaternary ammonium salts, iodides of alkali metals, such as sodium iodide, potassium iodide and elemental iodine. These iodinating agents are very easily removed after the reaction either by washing with water or with dilute sodium thiosulphate solution. Thus, the inventors were successful in reducing the undesired styrene impurity below regulatory limits and were able to obtain the desired condensation compound of formula (III) without any additional step of purification.

Literature references reveal that the prior art methods suggest alternative and tedious route of synthesis for preparation of intermediate (III). However, the present invention provides a simple method to suppress the styrene impurity by employing an iodinating agent.

The resulting fingolimod and its hydrochloride thus formed from intermediate (III) having styrene impurity below regulatory limits, were found to be conform to regulatory specification. Thus, an additional step of purification, which could considerably lower the yield, was avoided.

Scheme 1: Method for preparation of Fingolimod Hydrochloride (Ia)

Step-I

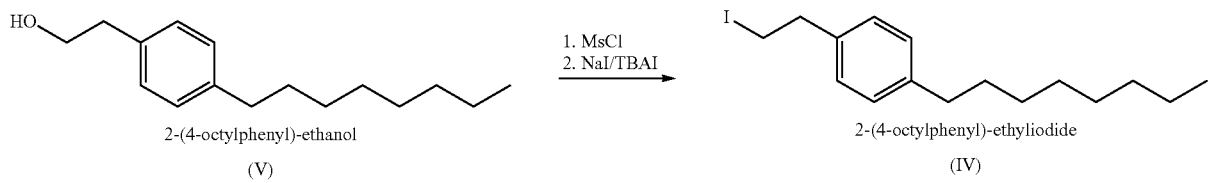

Step-II

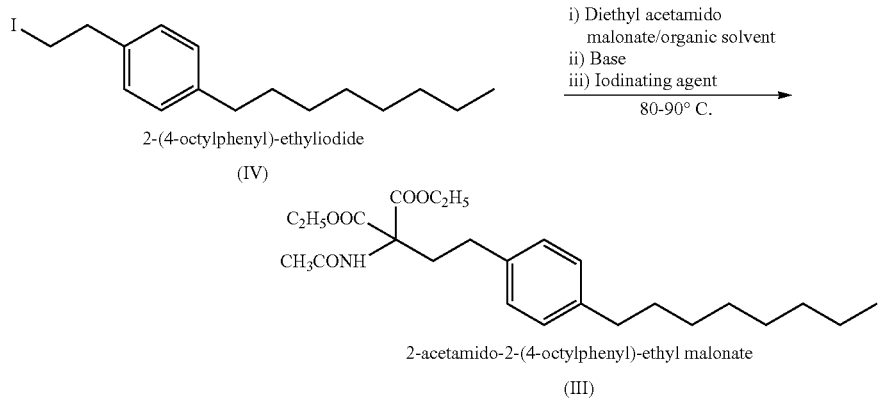

Step-III

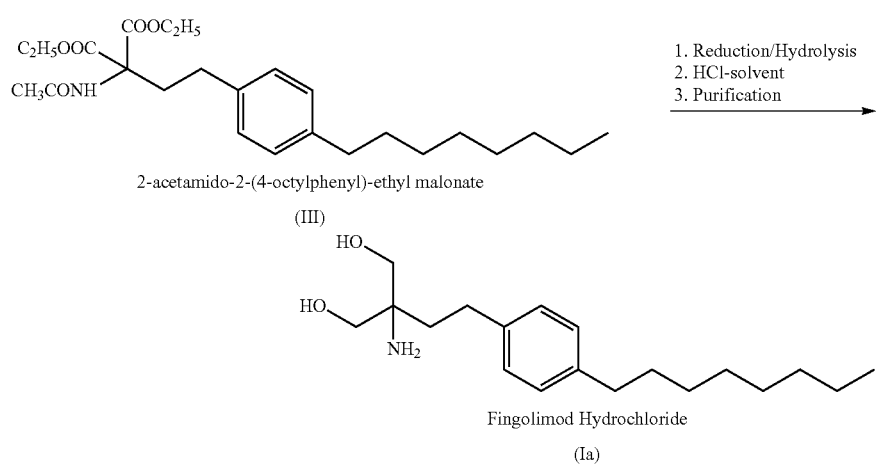

The detailed reaction process for preparation of fingolimod hydrochloride is described in the following steps:
1. reaction of 2-(4-octylphenyl)ethyl iodide (IV) with diethyl acetamidomalonate in presence of an iodinating agent and a base in an organic solvent to give diethyl 2-acetamido-2-(4-octylphenyl)ethyl malonate (III) of desired purity,
2. reduction of intermediate (III) to the corresponding alcohol formed in-situ followed by hydrolysis to fingolimod free base which is then finally converted to its hydrochloride salt, by treating with hydrochloric acid in an organic solvent.

2-(4-Octylphenyl)ethyl iodide (IV) was obtained by following methods known in the art (Ref.: U.S. Pat. No. 5,604,229, U.S. Pat. No. 6,605,744), which involved treatment of 2-(4-octylphenl)ethanol (V) with methane sulfonyl chloride and subsequent iodination with sodium iodide and a catalyst like quaternary ammonium iodide in a ketone solvent to yield compound (IV). The solvent was selected from the group comprising of acetone, methyl ethyl ketone, MIBK etc.

2-(4-Octylphenyl)-ethyl iodide (IV) was treated with diethyl acetamidomalonate in presence of a base and an iodinating agent in a solvent to give diethyl-2-acetamido-2-(4-octyl phenyl)ethyl malonate (III). The iodinating agent was selected from the group comprising of sodium iodide, potassium iodide, iodine, tetra butyl ammonium iodide (TBAI), preferably tetra butyl ammonium iodide (TBAI).

The organic solvent was selected from the group comprising of dimethylformamide, dimethyl sulfoxide, tetrahydrofuran and dimethylacetamide or mixtures thereof.

The base was selected from the group comprising of alkali metal carbonates like sodium carbonate, potassium carbonate, lithium carbonate, cesium carbonate etc.

The reaction mixture was heated between 80 and 90° C. till completion of reaction. The mixture was quenched with water and filtered. The solid separating out had impurity (II) in the range of 1-2%, which was then reduced to below 0.5% by recrystallization from a non-polar solvent like hexane to give compound of formula (III) having desired purity and with the undesired styrene impurity (II) below regulatory limits.

Without utilizing an iodinating agent, prior art methods resulted in formation of styrene impurity to an extent of 15 to 20%, which resulted in a loss of up to 42% in yield after purification. In stark contrast, the present inventors, by utilizing an iodinating agent were able to restrict the formation of styrene impurity below 2%, which could be easily removed during work up and isolation of intermediate (III).

The reduction of intermediate (III) to the corresponding alcohol was carried with sodium borohydride in presence of a metal halide like calcium chloride and in an organic solvent selected from alcohols such as isopropyl alcohol, methanol, dimethylformamide, dimethyl sulfoxide, tetrahydrofuran etc. Subsequent hydrolysis of the corresponding alcohol N-(2-(4-octylphenyl)ethyl-1,3-dihydroxypropan-2-yl)acetamide with an acid and alcohol as solvent provided fingolimod free base, which was converted to its hydrochloride salt by treating with hydrochloric acid in an alcohol. The alcohol was selected from the group comprising of methanol, ethanol, isopropyl alcohol etc.

Optionally, fingolimod free base was treated with a mixture of isopropyl alcohol and acetonitrile in the ratio of 1:1 to 1:4 and then subjected to treatment with hydrochloric acid in an alcohol to obtain the hydrochloride salt.

Fingolimod hydrochloride thus obtained was optionally purified by recrystallization to remove the isomeric impurity. The purification was carried out in an aqueous mixture of a ketone solvent. The ketone solvent was selected from the group comprising of acetone, methyl ethyl ketone and MIBK. The preferred aqueous ketone was a mixture of acetone and water in a proportion ranging from 99:1 to 75:25.

A further advantage of the invention is that the present invention did not utilize multiple crystallizations or column chromatography for purification of intermediate (III) or fingolimod free base (I) or its hydrochloride salt (Ia) as reported in prior art methods, which renders the present process cost effective.

The principles, preferred embodiments and modes of operation of the present invention have been described in the foregoing specification. The present invention is described herein below with reference to examples, which are illustrative only and should not be construed to limit the scope of the present invention in any manner.

EXAMPLES

Example 1

Preparation of 2-(4-octylphenyl)ethyl iodide (IV)

A mixture of 2-(4-Octylphenyl)ethanol (100 gms; 0.427 moles), dichloromethane (500 ml) and triethylamine (108 gms, 1.067 moles) were cooled between 0° C. and 5° C. Methanesulfonyl chloride (73.11 gms, 0.64 moles) was added gradually under nitrogen atmosphere and stirred for 2-5 hours between 0° C. and 30° C., till completion of the reaction based on TLC monitoring. The reaction mixture was quenched with water (500 ml) and organic layer after separation was concentrated under reduced pressure to yield the corresponding mesyl derivative, which was dissolved in methyl isobutyl ketone (1064 ml) containing tetrabutyl ammonium iodide (7.85 gms) and sodium iodide (139.7 gms). The reaction mixture was stirred for 3 hours and after completion of reaction, the mixture was quenched with water (665 ml) and the organic layer concentrated under reduced pressure to give 2-(4-octylphenyl)ethyl iodide (IV).

Yield: 150 gms (96.53%)

Example 2

Preparation of diethyl 2-acetamido-2-(4-octylphenyl) ethyl malonate (III)

Diethyl acetamidomalonate (59.86 gms), cesium carbonate (89.67 gm, 0.27 moles) and tetrabutyl ammonium iodide (21.42 gms; 0.05 moles) in DMSO (400 ml) were stirred at 25 to 30° C. 2-(4-Octylphenyl)ethyl iodide (IV) (100 gms, 0.29 moles) was gradually added to the reaction mixture under nitrogen atmosphere and stirred at 80 to 85° C. till completion of reaction. The reaction mixture was filtered, mixed with 1% potassium hydrogen sulfate solution, cooled to 0 to 5 C and filtered. The obtained solid was mixed with ethyl acetate and water was added to the mixture. Separation and concentration of the organic layer provided a residue containing 2-acetamido-2-(4-octylphenyl)ethyl malonate (III) which was crystallized from hexane.

Yield: 110.8 gms (88%);
Purity: 99.9%

Example 3

Preparation of Fingolimod Hydrochloride

2-Acetamido-2-(4-octylphenyl)ethyl malonate (III) (100 gms, 0.23 moles) was dissolved, in isopropyl alcohol and cooled to 5-10° C. Sodium borohydride (43.8 gms) and calcium chloride (55.0 gms) were gradually added below 10° C. and stirred for 3-4 hours at 25 to 30° C. After completion of reaction, based on TLC, the reaction mixture was quenched with water and extracted with ethyl acetate (700 ml). The organic layer was concentrated under reduced pressure and the residue treated with hydrochloric acid dissolved in isopropyl alcohol and stirred for 2-3 hours at 80 to 100° C. The reaction mixture was cooled to 5-10° C., quenched with sodium carbonate solution (20%) and extracted with ethyl acetate. The organic layer was concentrated under reduced pressure to yield a residue containing fingolimod free base.

Isopropyl alcohol containing hydrochloride acid was added to the residue and stirred for 1 hour. The mixture was stirred at 5-10° C., filtered, washed with isopropyl alcohol and dried.

Yield: 59.4 gms (75%); Purity: 99.91%

Example 4

Purification of Fingolimod Hydrochloride

Fingolimod hydrochloride (50 gms, 0.1 mole) was dissolved in acetone (1600 ml) and stirred for 1-2 hours at 55-55° C. Water (25 ml) was added at 50-55° C. and stirred for 1 hour. The mixture was cooled to 25-30° C., and the solid separating out was filtered and dried.

Yield 46 gm, (92%); Purity: 99.98%; Isomeric impurity: 0.01%.

We claim:

1. A process for the preparation of fingolimod hydrochloride of formula (Ia) comprising (Ia)

·HCl (i) reacting 2-(4-octylphenyl)ethyl iodide with diethyl acetamidomalonate in the presence of a base and an iodinating agent selected from quaternary ammonium iodide salts, alkali metal iodide salts, and any combination thereof, in a solvent to give diethyl 2-acetamido-2-(4-octylphenyl) ethyl malonate;

(ii) reducing the diethyl 2-acetamido-2-(4-octylphenyl) ethyl malonate;

(iii) hydrolyzing the resulting product to give fingolimid base; and (iv) converting the fingolimod base to fingolimod hydrochloride.

2. The process as claimed in claim 1, wherein the iodinating agent is selected from sodium iodide, potassium iodide, tetrabutyl ammonium iodide, and any combination thereof.

3. The process as claimed in claim 1, wherein the solvent is selected from dimethylformamide, dimethyl sulphoxide, tetrahydrofuran, diethyl acetamide, and any combination thereof.

4. The process as claimed in claim 1, wherein the base is an inorganic base.

5. The process as claimed in claim 1, wherein step (iv) comprises (i) treating the fingolimod base with hydrochloric acid in an alcohol solvent to give fingolimod hydrochloride, (ii) dissolving the fingolimod hydrochloride in aqueous acetone; and (iii) recrystallizing the fingolimod hydrochloride from the aqueous acetone to give fingolimod hydrochloride free from styrene impurity (II) and isomeric impurity (Ib)

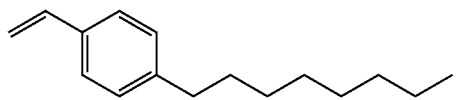

(II)

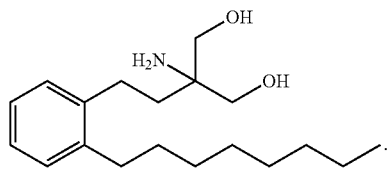

(Ib)

6. The process as claimed in claim 1, wherein the fingolimod hydrochloride contains below 0.5% of styrene impurity (II) and below 0.5% of isomeric impurity (Ib)

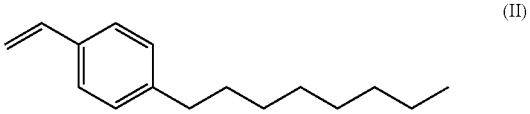

(II)

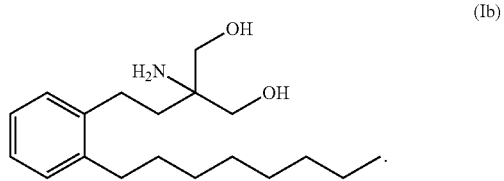

(Ib)

7. The process as claimed in claim 4, wherein the inorganic base is selected from sodium carbonate, lithium carbonate, cesium carbonate, and any combination thereof.

8. The process as claimed in claim 1, wherein in step (ii) the 2-acetamido-2-(4-octylphenyl) ethyl malonate is reduced with sodium borohydride.

9. The process as claimed in claim 1, wherein in step (iii) the resulting product is hydrolyzed with a mineral acid.

10. The process as claimed in clam 5, wherein in step (ii) the fingolimod hydrochloride is dissolved in aqueous acetone at 50-55° C.

* * * * *